United States Patent [19]

Di Toro et al.

[11] Patent Number: 4,501,916
[45] Date of Patent: Feb. 26, 1985

[54] PROCESS FOR PREPARING ALKYL ESTERS OF C-ALKYL-TARTRONIC OR C-HALOGENALKYL-TARTRONIC ACIDS

[75] Inventors: Vincenzo Di Toro, Como; Franco Gozzo; Pier M. Boschi, both of San Donato Milanese, all of Italy

[73] Assignee: Montedison S.p.A., Milan, Italy

[21] Appl. No.: 338,620

[22] Filed: Jan. 11, 1982

[30] Foreign Application Priority Data

Jan. 12, 1981 [IT] Italy ............................ 19088 A/81

[51] Int. Cl.³ .................... C07C 67/02; C07C 67/22
[52] U.S. Cl. .................................................. 560/180
[58] Field of Search ...................... 560/180; 562/582; 260/453.7

[56] References Cited

U.S. PATENT DOCUMENTS

| | | | |
|---|---|---|---|
| 2,042,458 | 6/1936 | Crawford | 560/215 |
| 2,337,858 | 12/1943 | Stoesser | 560/204 |
| 3,488,385 | 1/1970 | Marangoni et al. | 562/582 |
| 3,950,397 | 4/1976 | Batelaan | 560/180 |
| 4,310,470 | 1/1981 | Adams | 260/453.7 |

OTHER PUBLICATIONS

March, J. *Advanced Organic Chemistry, Reaction Mechanisms and Structure*, Intern. Stud. Ed., McGraw–Hill, Kogakusha (1968), at p. 323.

Roger, Robert et al., *Chemical Reviews*, vol. 61 (1961), at pp. 181 and 191.

Kirk–Othmer *Encyclopedia of Chemical Technology* 2nd Ed., vol. 8 (1966), Interscience, Publ. pp. 356–357.

Hackh's *Chemical Dictionary* 4th Ed. (1969), McGraw-Hill, Publ. pp. 41–42, 117–118, 249–250, 424–425 and 548–549.

*Primary Examiner*—Natalie Trousof
*Assistant Examiner*—L. Hendriksen

[57] ABSTRACT

A process is herein described for obtaining lower alkyl esters of C-alkyl-tartronic or C-halogenalkyl-tartronic acids according to the reaction:

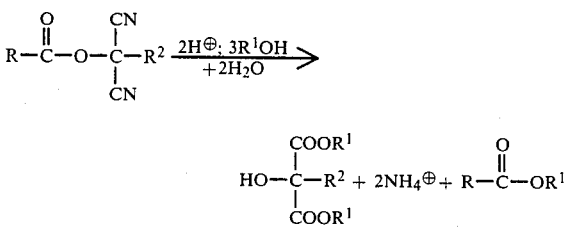

in which R and $R^2$, like or unlike each other, may be alkyls having $C_1$–$C_5$ or halogenalkyls having $C_1$–$C_5$ and $R^1$ is an alkyl having $C_1$–$C_5$.

6 Claims, No Drawings

PROCESS FOR PREPARING ALKYL ESTERS OF C-ALKYL-TARTRONIC OR C-HALOGENALKYL-TARTRONIC ACIDS

THE PRIOR ART

Among the esters of lower alkyls of C-alkyl-tartronic acids, the diethyl ester of C-methyl-tartronic acid is known from the article by Eskola and Mountinen published in Suomen Kemistilehti (20 B-1947-page 18). The Authors obtain the diethyl ester of the C-methyl-tartronic acid from the diethyl ester of the methyl-malonic acid by oxidation with $KMnO_4$. By a similar method also the other esters are preparable, but with low yields. A process for preparing the esters of the citramalic acid, α-methyl-β-alkyl-malic acid, methyltartronic acid and α-alkyl-β-alkoxylactic acid starting from the corresponding cyanhydrins was found by J. Cologne, L. Watteau and L. Cumet (see Bulletin de la Société Chimique de France 1947, pages 245–247): such method, however, is affected by the drawbacks of not being employable for preparing the methyl, ethyl and propyl esters of the C-alkyl-tartronic acid due to the low yields, and of not providing high yields in the preparation of the starting cyanhydrin (32% of cyanhydrin of butyl pyruvate). An even more serious drawback of this process when utilized for preparing alkyl tartronates resides in the necessity of starting from very expensive starting materials, such as the pyruvates.

THE PRESENT INVENTION

Since the esters of lower alkyls of C-alkyl- or C-halogenalkyl-tartronic acids are diffusely used in the preparative organic chemistry as useful intermediates in the preparation of aminoacids, of barbiturics, of oxazolidine derivatives, etc., It was necessary to find a process which might permit to obtain the alkyl esters of C-alkyl- and C-halogenalkyl-tartronic acids with high yields, starting from products which are easily obtainable with high yields and at low cost.

it is an object of the present invention to provide a simple method of producing esters of lower alkyls of C-alkyl- and C-halogenalkyl-tartronic acids with high yields.

Another object is that of providing a process as mentioned hereinbefore starting from intermediates, which, in turn, are obtainable with high yields from starting materials available at low cost on the market.

These and still other objects are achieved by the process according to the present invention, which consists in treating the alkanoic ester of a 1-hydroxy-1,1-dicyano-alkane optionally substituted by halogen in the $C_1$–$C_5$ alkyl portion (I) with a lower alcohol R'OH, such as for example methyl, ethyl, propyl, butyl or pentyl alcohol in such a molar excess that the ratio between lower alcohol and ester of the dicyano alcohol may range from 4 to 10 (preferably 7) in the presence of a strong mineral acid in an at least stoichiometric amount and preferably in excess up to a molar ratio between acid and ester of the dicyanoalcohol equal to 4, under fully anhydrous conditions and at temperatures in the range of from 0° to 20° C.; the reaction mixture is then treated with a water amount equal to about 2 moles per mole of ester of the starting dinitrile and is heated to the boiling temperature, while distilling a mixture of vapours of alcohol and of ester of the aliphatic monocarboxylic acid until 15%–30% by weight of the whole mixture is removed. A dialkyl-ester of the C-alkyl (or C-haloalkyl)-tartronic acid of general formula III with high yields, generally higher than 75%, is so obtained.

The reaction is supposed to occur in at least two consecutive steps as follows:

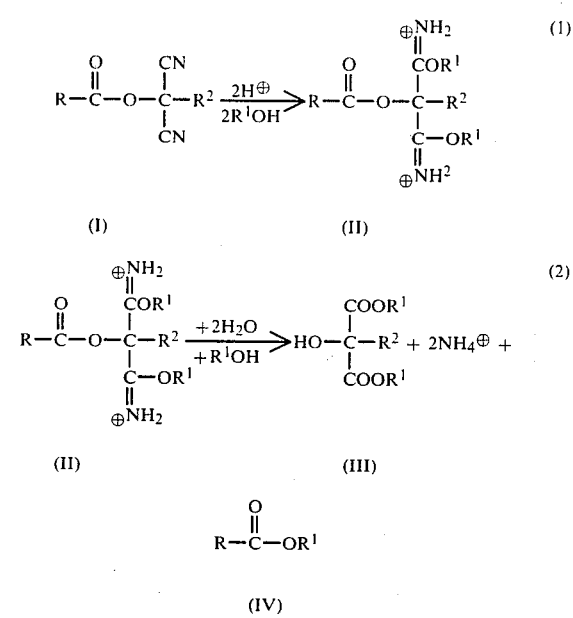

(wherein R and $R^2$, like or unlike each other, may be alkyls or halogenalkyls having $C_1$–$C_5$ and $R^1$ is an alkyl having $C_1$–$C_5$).

The forming of imidoesters II (reaction 1) shall occur in anhydrous conditions. The acids utilized in this reaction are generally gaseous HCl or $H_2SO_4$.

In the latter case, the commercially available sulphuric acid at 96% may be advantageously anhydrified by addition of oleum: a sufficient amount of oleum may also permit the anhydrification of the alcohol.

In reaction 2 it is important—after the addition of water and during the alcoholysis of the ester of the tertiary alcohol—to distill a portion of compound IV which forms as reaction by-product.

At the conclusion of the reaction, the mixture is cooled down, the ammonium salt which has formed is separated by filtration and the dialkyl ester of the C-alkyl (or C-haloalkyl)-tartronic acid is isolated by vacuum distillation. The dialkyl esters of the C-alkyl-tartronic acids are tertiary alcohols. The high yields obtained, according to the process of this invention, in the preparation of a series of these hydroxy-esters, are surprising in consideration of the impossibility of carrying out, in most of cases, a transesterification of esters of tertiary alcohols.

In this connection it is interesting to observe the different trend of the alcoholysis reactions concerning esters of tertiary alcohols and described in J. March "Advanced Organic Chemistry, Reaction Mechanisms, and Structures", Mc. Graw-Hill Kogakusha 1968, page 323, lines 5–8, by Intern. Stud. Edition.

Thus, it is possible to obtain, by this process, the C-alkyl (or halogenalkyl)-tartronic esters of general formula III listed in the following Table.

It is to be appreciated that the following examples are given for illustrative, but not limitative purposes. It is apparent, in fact, that the process herein described may be extended to compounds containing a great variety of groups $R^1$ and $R^2$ consistent with the functional groups present in the structure of formula III.

TABLE

C—alkyl- or C—halogenalkyl-tartronic esters of general formula:

$$R^2-\underset{\underset{COOR^1}{|}}{\overset{\overset{COOR^1}{|}}{C}}-OH$$

| | $R^2$ | $R^1$ | boiling point |
|---|---|---|---|
| (1) | $CH_3$ | $CH_3$ | 101°–103° C./15 mm Hg |
| | | | 75° C./2 mm Hg |
| (2) | $CH_3$ | $C_2H_5$ | 107°–110° C./14 mm Hg |
| (3) | $CH_3$ | $n.C_3H_7$ | 128°–130° C./18 mm Hg |
| | | | 80° C./0.2 mm Hg |
| (4) | $CH_3$ | $i.C_3H_7$ | 104°–105 C./18 mm Hg |
| (5) | $C_2H_5$ | $CH_3$ | 102°–104 C./15 mm Hg |
| (6) | $C_2H_5$ | $C_2H_5$ | 110° C./15 mm |
| (7) | $C_2H_5$ | $n.C_3H_7$ | 120°–123° C./18 mm |
| (8) | $CH_2Br$ | $C_2H_5$ | 154° C./25 mm Hg |

The following examples are given to better illustrate the process of the present invention.

EXAMPLE 1

Preparation of diethyl-2-methyl-tartronate (compound No. 2 in the Table).

$$\underset{\underset{CN}{|}}{\overset{\overset{CN}{|}}{CH_3-C}}-O-\overset{\overset{O}{\|}}{C}-CH_3 \xrightarrow{HCl/C_2H_5OH;\ H_2O} \underset{\underset{COOC_2H_5}{|}}{\overset{\overset{COOC_2H_5}{|}}{CH_3-C}}-OH$$

M.W. 138,124  M.W. 36,465  M.W. 46,048  M.W. 18  M.W. 190,193

1          2           3            4

1 100 g = 0.72 moles
2 100 g = 2.74 moles
3 300 ml = 5.14 moles
4 26 g = 1.44 moles In a 1-liter flask, hydrochloric acid was dissolved in anhydrous ethanol at 0°–10° C.

The resulting solution was cooled with ice and salt, whereupon dinitrile 1 was added in such a way that the temperature was maintained in the range from 0° to 5° C. It was stirred for 3 hours at 0° C., then the temperature was allowed to rise up to room temperature, and the solution was then allowed to rest overnight. $H_2O$ was made to drop and it was heated at partial reflux for 4 hours, while distilling about 20% of the solution: in the meantime a solid product formed which consisted of $NH_4Cl$ that was filtered and washed with ethyl alcohol and the solution was then evaporated at reduced pressure.

The residue was poured into 50 ml of $H_2O$ and was extracted five times with 50 ml each of $CH_2Cl_2$.

The solution was dried on anhydrous $Na_2SO_4$ and the solvent was removed by evaporation at reduced pressure.

By pump distillation with $H_2O$ there were obtained 113 g of 2-methyl-diethyl-tartronate having a purity (determined by gas chromatographic analysis) of 98%.

Elemental analysis: consistent with the formula
Yield = 82.1%.

I.R. characterization film:
  $\gamma(OH) = 3,490$ cm$^{-1}$;
  $\gamma(C=O) = 1,740$ cm$^{-1}$.

N.M.R. characterization CD $Cl_2$/TMS:

$\delta = 1.4$ ($CH_2$—$CH_3$:tripl.);
$\delta = 1.7$ (sing.$\underline{CH_3}$ in position $\alpha$);
$\delta = 4.3$ (quadr. $\underline{CH_2}$);
$\delta = 4.5$ (OH).

EXAMPLE 2

Preparation of 2-methyl-2-hydroxydiethyl-malonate (or diethyl-methyl-tartronate) (Compound No. 2 in the Table).

$$\underset{}{\overset{CN\ \ \ \ CN}{\times}} \ \ \overset{\overset{O}{\|}}{\underset{O}{C}} \xrightarrow{H_2SO_4/C_2H_5OH;\ H_2O} \overset{COOEt}{\underset{COOEt}{\times}}OH$$

M.W. 138,124  M.W. 98,07  M.W. 46,978  M.W. 18,016  M.W. 190,193. To a solution containing 2.17 moles of $H_2SO_4$, obtained by mixing 300 ml of anhydrous $C_2H_5OH$, 61.4 ml of 96% $H_2SO_4$ and 52.8 ml of fuming $H_2SO_4$ at 20% of $SO_3$, there were added, at 0° C., 0.72 moles of 1-acetoxy-1,1-dicyano-ethane (98.4 g).

The reaction mixture was maintained under stirring at 0° C. for 3 hours. It was allowed to reach the room temperature, 1.4 moles of $H_2O$ were added and it was boiled at partial reflux for 5 hours, removing by distillation 30% by weight of the reaction mixture. Forming of $(NH_4)HSO_4$ was observed.

The solid was filtered, washed with $C_2H_5OH$, and the solution was concentrated at reduced pressure.

The residue was poured into 100 ml of $H_2O$ and the acid solution was neutralized by addition of $Na_2CO_3$.

It was extracted with $CH_2Cl_2$, it was anhydrified on $Na_2SO_4$ and then concentrated. By distillation under reduced pressure 103 g of 2-methyl-2-hydroxy-diethyl malonate (110° C./15 mm Hg) were obtained. Yield = 76%.

EXAMPLE 3

Preparation of diethyl-methyl-tartronate (Compound No. 2 in the Table).

A solution containing 2.17 moles of $H_2SO_4$, prepared by mixing 120 ml of anhydrous $C_2H_5OH$, 183.15 ml of 95° $C_2H_5OH$ and 107.1 ml of fuming $H_2SO_4$ at 20% of $SO_3$, was additioned at 0° C. with 98.4 g (0.72 moles) of 1-acetoxy-1,1-dicyano-ethane. It was then operated as in example 2 and the same results were obtained.

EXAMPLE 4

Preparation of dimethyl-ethyl-tartronate (Compound No. 5 in the Table).

$$\underset{CN\ \ \ \ CN}{\times} \ \ \overset{\overset{O}{\|}}{\underset{O}{C}} \xrightarrow{HCl/CH_3OH;\ H_2O} \overset{COOCH_3}{\underset{COOCH_3}{\times}}OH$$

M.W. 166,177  M.W. 36,5  M.W. 32,04  M.W. 18,016  M.W. 176,167

1          2         3           r 1 24 g = 0.145 moles                           $(C_7H_{12}O_5)$
2 12 g = 0.3 moles
3 50 ml
4 5.4 g = 0.3 moles 1-propionoxy-1,1-dicyano-propane (reagent 1, dimer of proprionyl cyanide) was added, in small lots, to the methanol solution of HCl, so that the temperature did not exceed 0° C.

It was stirred for 3 hours at 0° C., whereupon the temperature was allowed to reach 15°–20° C.

After addition of $H_2O$, the reaction mixture was boiled for 4 hours, distilling 15% by weight.

The precipitated $NH_4Cl$ was filtered, washed with $CH_3OH$ and the solution was evaporated at reduced pressure; the residue was poured into 50 ml of $H_2O$ and extracted with 100 ml (4 times) of $CH_2Cl_2$.

After evaporation of the solvent and distillation, by water pump, of the residual oil, 20.6 g of product, having a boiling point of 101°–103° C./15 mm Hg, were obtained.

Yield = 80.7%.

N.M.R. characterization $CDCl_3$/TMS:

$\delta = 0.95$ (tripl. $CH_2$—$CH_3$);
$\delta = 2.1$ (quadr. $CH_2$—$CH_3$);
$\delta = 3.75$ (sing. $CH_3$)
$\delta = 4$ (OH)

The compounds listed on the Table were prepared according to methods analogous with the ones described in examples 1 to 4.

What is claimed is:

1. A process for preparing the alkyl esters of acids selected from the group consisting of C-alkyl tartronic acids and C-halogenalkyl tartronic acids in which the alkanoic ester of a 1-hydroxy-1,1-dicyano-alkane or a 1-hydroxy-1,1-dicyano-alkane substituted by a halogen in the $C_1$–$C_5$ alkyl part is reacted with an alcohol R'OH wherein R' is a $C_1$–$C_5$ alkyl, in a molar ratio between alkanoic ester and lower alcohol of from 1:4 to 1:10 at 0° C. to 20° C. under anhydrous conditions and in the presence of a strong mineral acid, the molar ratio of acid to alkanoic ester being from 1:1 to 4:1, combined with hydrolyzing the resulting imido ester with two moles of water per mole of ester of the starting dinitrile, at the boiling temperature of the reaction mixture, while distilling to remove 15 to 30% by weight of the reaction mixture, and working up the solid mixture according to conventional techniques to isolate the alkyl ester of C-alkyl or C-halogenalkyl tartronic acid.

2. The process according to claim 1, in which the strong mineral acid is $H_2SO_4$.

3. The process according to claim 2, in which, to sulphuric acid having a titer below 100%, there is added a sufficient amount of oleum to dehydrate it and to dehydrate the alcohol in which the reaction occurs.

4. The process according to claim 1, in which the strong mineral acid is HCl.

5. The process according to claim 1, in which the alcohol/dinitrile molar ratio is equal to 7.

6. The process according to claim 1, in which after or during the hydrolysis with water about 20% by weight of the mixture is removed by distillation.

* * * * *